United States Patent [19]

Hattori et al.

[11] 4,306,444
[45] Dec. 22, 1981

[54] AIR-FUEL RATIO DETECTING SYSTEM

[75] Inventors: Tadashi Hattori, Okazaki; Yoshiki Ueno, Aichi, both of Japan

[73] Assignee: Nippon Soken, Inc., Nishio, Japan

[21] Appl. No.: 100,383

[22] Filed: Dec. 5, 1979

[30] Foreign Application Priority Data

Dec. 7, 1978 [JP] Japan .............................. 53-152337

[51] Int. Cl.³ .......................................... G01N 27/12
[52] U.S. Cl. ....................................... 73/23; 123/440
[58] Field of Search .................... 73/23; 123/440, 489; 60/276, 285

[56] References Cited

U.S. PATENT DOCUMENTS 4,112,893 9/1978 Anzai ...................................... 73/23
4,237,839 12/1980 Ueno et al. ........................... 123/440

*Primary Examiner*—Stephen A. Kreitman

[57] ABSTRACT

An air-fuel ratio detecting system having a resistor device in series with an oxygen detector element with the electrical resistance thereof changing with the oxygen component of the exhaust gas from an automobile engine, wherein a constant voltage is applied to the series circuit, and by means of the voltage at the junction point of the oxygen detector element and the resistor device the air-fuel ratio of the mixture is detected. The system comprises a sample circuit which detects the voltage at the junction point of the oxygen detector element and the resistor device when the air-fuel ratio is at a predetermined value on either rich or lean side, and a comparator which compares the output of the sample circuit with a predetermined reference voltage, wherein the resistance value of the variable resistors is changed in accordance with the result of comparison, and erroneous detection of the oxygen concentration is prevented even when the resistance characteristic of the air-fuel ratio sensor changes by the change of the working temperature or by lapse of time.

2 Claims, 13 Drawing Figures

AIR-FUEL RATIO DETECTING SYSTEM

BACKGROUND OF THE INVENTION

The present invention relates to an air-fuel ratio detecting system or more in particular to a system for detecting the air-fuel ratio from the exhaust gas components produced from the engine.

Conventionally it has been proposed, as a system for detecting the air-fuel ratio from the engine exhaust gas components, e.g., an oxygen concentration, such system in which an air-fuel ratio sensor essentially comprising a metal oxide semiconductor such as titania $TiO_2$ for exhibiting an electrical resistance depending on the oxygen concentration is connected with a fixed resistor for voltage division or a dividing resistor, and the voltage at the junction point thereof is compared with a reference voltage by a comparator circuit, and thereby it is detected whether the actual air-fuel ratio is higher (lean) or lower (rich) than the stoichiometric air-fuel ratio.

In the conventional system such as the above, however, the dividing resistor is set at a fixed value and therefore when the electrical resistance Re characteristics of the air-fuel sensor shifts from curve X (working temperature of 500° C.) to curve Y (working temperature of 800° C.) in FIG. 1 in accordance with the working temperature or by lapse of time, the accuracy of air-fuel detection is reduced, often leading to an erroneous detection.

The voltage $V_A$ at the junction point of the air-fuel ratio sensor and the fixed resistor, for example, changes along the curve X in FIG. 2 at the working temperature of 500° C., and the crossing thereof with the reference voltage Vs shown by the solid line represents the stoichiometric air-fuel ratio ST, thus making it possible to detect whether the air-fuel ratio is higher or lower than the stoichiometric air-fuel ratio ST.

When the electrical resistance characteristic of the air-fuel sensor changes in accordance with the working temperature thereof or by lapse of time, the voltage $V_A$ changes, for instance, as shown by curve Y in FIG. 2, and the crossing with the reference voltage Vs is displaced to the lean side from the stoichiometric air-fuel ratio ST by $\Delta A/F$, thus it causes an error in the detection of the air-fuel ratio. In an extreme case, the crossing between the voltage $V_A$ and reference voltage Vs disappears, thus making it impossible to detect the air-fuel ratio.

SUMMARY OF THE INVENTION

The present invention is made in view of the above-mentioned facts and an object of this invention is to provide an air-fuel detecting system capable of detecting the air-fuel ratio satisfactorily irrespective of the change of the characteristic of the air-fuel ratio sensor by change of the working temperature or by lapse of time.

In particular, according to the present invention, the voltage at the junction point of the air-fuel ratio sensor and the resistor for voltage division is detected at a predetermined point in either one of the rich or lean side, and in accordance with the voltage value as detected above, the electrical resistance of the dividing resistor is changed, thus preventing the accuracy of detecting the air-fuel ratio from being reduced or an detection error.

DESCRIPTION OF THE PREFERRED EMBODIMENT

Figure 4:
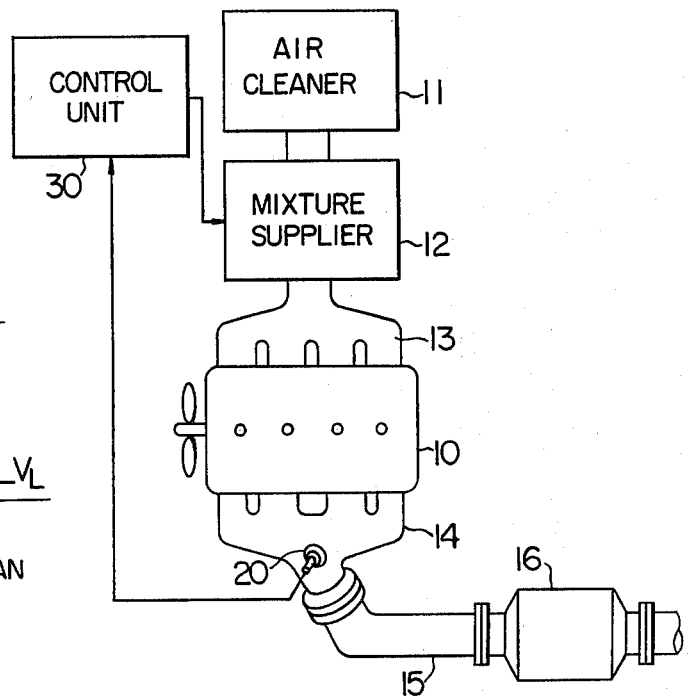
FIG. 4 is a diagram showing the general configuration of the system to which the present invention is applied.

The embodiments of the present invention shown in the drawings will be explained below. In FIG. 4 showing a system to which the present invention is applied, an engine 10 is a well known engine of spark ignition type using gasoline or LPG as a fuel. The intake system of this engine comprises an air cleaner 11, a mixture supplier 12, and an intake manifold 13. The exhaust system thereof, on the other hand, comprises an exhaust manifold 14, an exhaust tube 15, a ternary catalyst converter 16 for purification of the exhaust gas and a noise-damping muffler not shown in the drawing.

The mixture supplier 12 includes a fuel injector or a carburetor having a well known electronic air-fuel ratio regulator for changing the air-fuel ratio of the mixture gas (at intake system) in response to an electrical signal. The ternary catalyst converter 16 is for eliminating NOx, HC and CO at the same time at high efficiency upon application of the mixture gas having an air-fuel ratio almost equal to the stoichiometric value thereof to the engine 10 and contains a well known catalyst in the form of pellet or honeycomb.

Next, the air-fuel ratio detector will be explained. The air-fuel ratio detector comprises an air-fuel ratio sensor 20 arranged at the merging point of the exhaust manifold 14 and a control unit 30 for applying an electrical signal to the mixture gas supplier 12.

Figure 5:
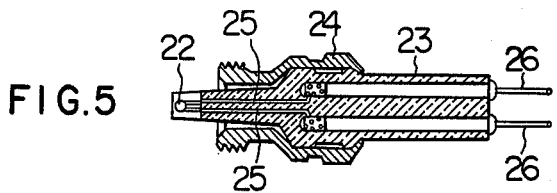
FIG. 5 is a sectional view showing the air-fuel ratio sensor of FIG. 4.

The air-fuel ratio sensor 20 is constructed as shown in FIG. 5. In FIG. 5, a disc-shaped element 22 for detecting the gas components of the exhaust gas, or especially, the oxygen concentration thereof, and having an electrical resistance changing stepwise with the air-fuel ratio is made of a metal oxide semiconductor such as titania ($TiO_2$) and carries on the surface thereof a catalyst such as platinum or rhodium. The element 22 is held at the forward end of the support 23 of a heat-resistant electrical insulating member made of a sintered material of aluminum or the like. The support 23 is coupled with a heat-resistant metal housing 24 and mounted on the exhaust manifold 14 with the screw of the housing 24.

Two platinum electrodes 25 arranged inside of the support 23 are inserted into the element 22, and the electrodes 25 are electrically connected to terminal rods 26 respectively via conductive glass. Thus the electrical resistance value of the element 22 is indicated through the terminal rods 26.

Figure 1:
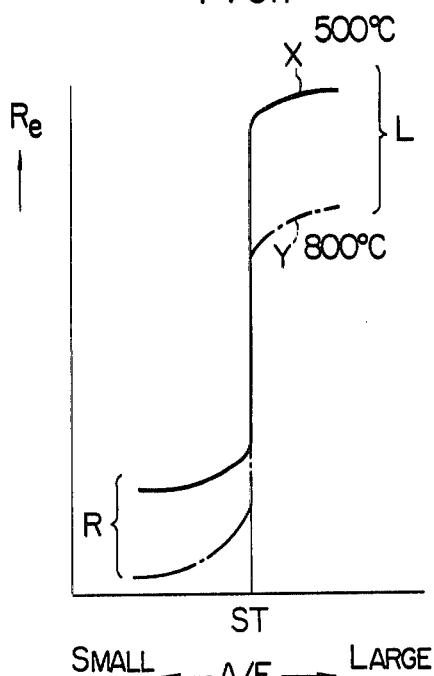
FIG. 1 is a graph showing the electrical resistance characteristic of the air-fuel ratio sensor.
Figure 2:
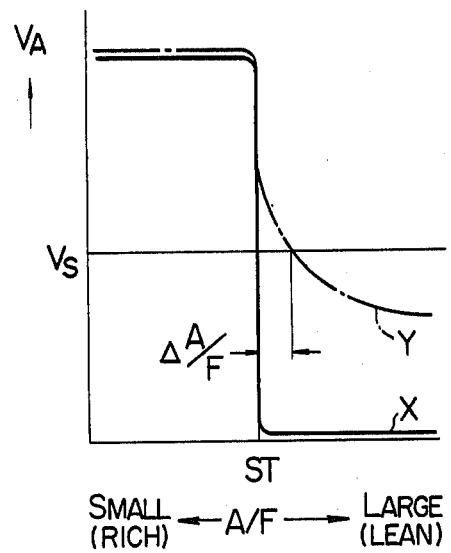
FIG. 2 is a graph showing the voltage characteristic changing with the characteristic of the air-fuel ratio sensor.

The air-fuel ratio sensor 20 has an electrical resistance Re which changes in accordance with the air-fuel ratio as shown in FIG. 1. In the case where the air-fuel ratio is higher than the stoichiometric value ST (lean), the resistance of the air-fuel ratio sensor becomes the lean resistance value L. When the air-fuel ratio is smaller than the stoichiometric value ST (rich), on the other hand, the resistance of the air-fuel sensor becomes a rich resistance value R. This electrical resistance value characteristic varies in accordance with the change of the working temperature or by lapse of time as shown by curves X and Y in FIG. 1.

Figure 6:
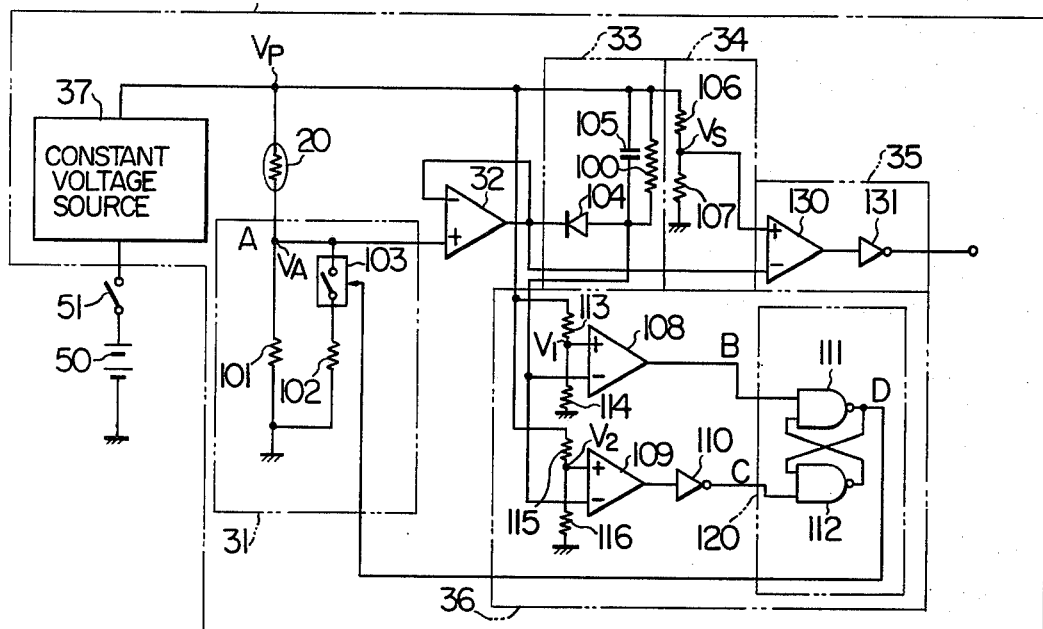
FIG. 6 is a diagram showing an electrical circuit of an embodiment of the present invention.

The construction of the control unit 30 will be explained below with reference to FIG. 6. A constant-voltage source 37 is supplied with a power through a key switch 51 from a battery 50 and produces a constant DC voltage Vp. An end of the constant-voltage source 37 is connected to the air-fuel ratio sensor 20. The dividing resistor 31 connected in series to the air-fuel ratio sensor 20 through the junction point A includes two dividing resistors 101 and 102 each of which has an end grounded. The dividing resistor 101 is always connected to the air-fuel ratio sensor 20, while the other dividing resistor 102 is connected through an analog switch 103 to the air-fuel ratio sensor 20.

The switch 103 is of well-known type which is turned on in response to application of a "1" level signal and is turned off in response to application of a "0" level signal.

The buffer amplifier 32 is supplied with the voltage $V_A$ of the junction point A for amplifying the current while maintaining the voltage constant, thus accomplishing an impedance conversion. The peak sample circuit 33 includes a resistor 100, a diode 104 and a capacitor 105 for holding and storing the output voltage of the buffer amplifier 32, i.e., the voltage $V_A$ at the junction point A for a certain period of time.

The voltage generator circuit 34 comprises resistors 106 and 107. By setting the resistors 106 and 107 at a predetermined value, a predetermined reference voltage Vs is applied to the non-inverted terminal of the comparator 130.

The control circuit 36 comprises comparators 108 and 109, a NOT circuit 110, NAND circuits 111 and 112 constituting an R-S flip-flop 120, and resistors 113 to 116. The resistors 113 and 114 are connected in series with each other, and the voltage V1 is produced from the junction point thereof. In a similar way, the resistors 115 and 116 are connected in series with each other, thus producing the voltage V2 from the junction point thereof.

The comparator 108 compares the voltage V1 with the minimum value detected by the peak sample circuit 33, and produces a "0" level signal, thus causing the flip-flop 120 to produce a "1" level signal, if the minimum value is larger than the voltage V1.

The comparator 109 compares the voltage V2 with the minimum value detected by the peak sample circuit 33, and if the minimum value is lower than the voltage V2, the comparator produces a "1" level signal, so that the output of the flip-flop 120 is raised to "1" through the NOT circuit 110. The flip-flop 120 is connected with the switch 103, which is subjected to on-off control by the output of the flip-flop 120.

The comparator circuit 35 is supplied with the reference voltage Vs set by the voltage generator circuit 34 and the voltage $V_A$ at the junction point A. The comparator 130 compares the reference voltage Vs with the voltage $V_A$, and produces a rich signal of "1" level through the NOT circuit 131 when the voltage $V_A$ is higher. When the voltage $V_A$ becomes smaller than the reference voltage Vs, the comparator 130 produces a lean signal of "0" level.

In the above configuration, the electrical resistance value of the air-fuel ratio sensor 20 changes in accordance with the components of the exhaust gas discharged from the engine 10, especially, the oxygen concentration thereof. The components of the exhaust gas changes in accordance with the air-fuel ratio of the mixture gas supplied from the mixture gas supplier 12 to the engine 10, and therefore the electrical resistance Re of the air-fuel ratio sensor 20 changes in accordance with the air-fuel ratio as shown in FIG. 1.

In other words, the resistance of the air-fuel ratio sensor 20 becomes lean resistance value L when the air-fuel ratio is higher than the stoichiometric value ST (14.7), and becomes rich resistance value R when the air-fuel ratio is lower than the stoichiometric value ST thereof.

Figure 8:
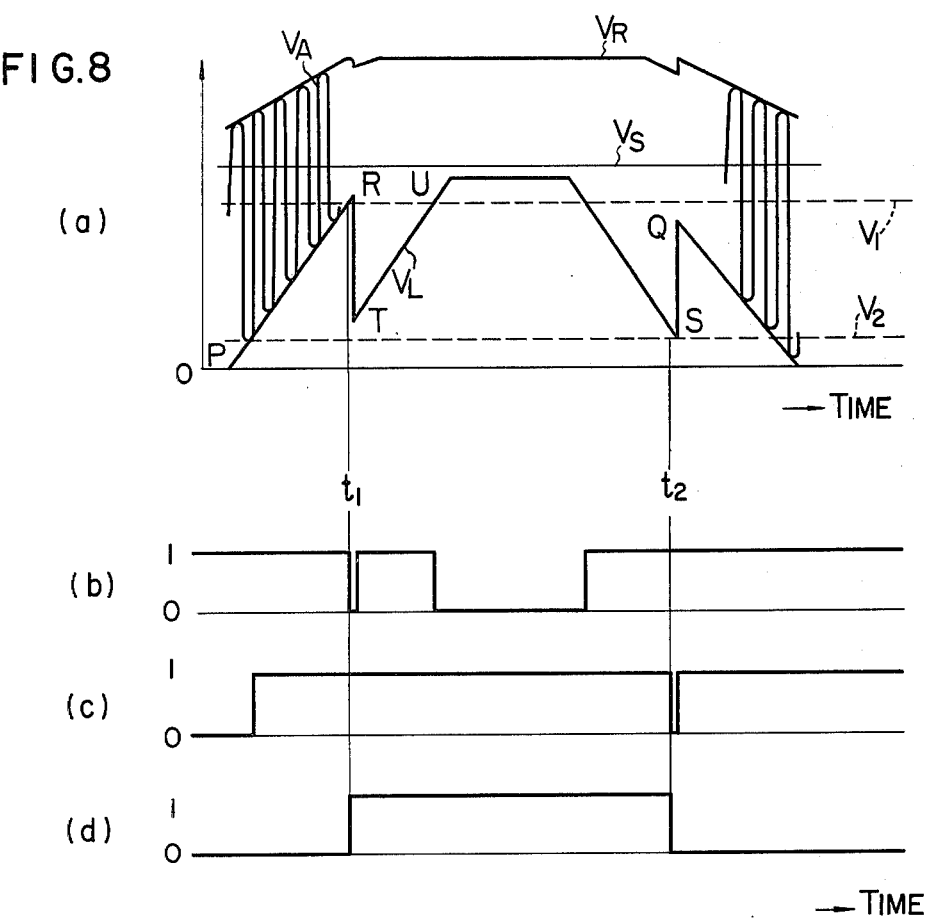

The voltage $V_A$ at the junction point A depends on the electrical resistance value Re of the air-fuel ratio sensor 20 and $V_A$ becomes to be of a low level value when the resistor of the air-fuel ratio sensor 20 has the lean resistance value L and it becomes of a high level value when the resistance of the sensor 20 has the rich resistance value R, thus the voltage of the junction point A changes as shown by $V_A$ in FIG. 8(a).

Figure 7:
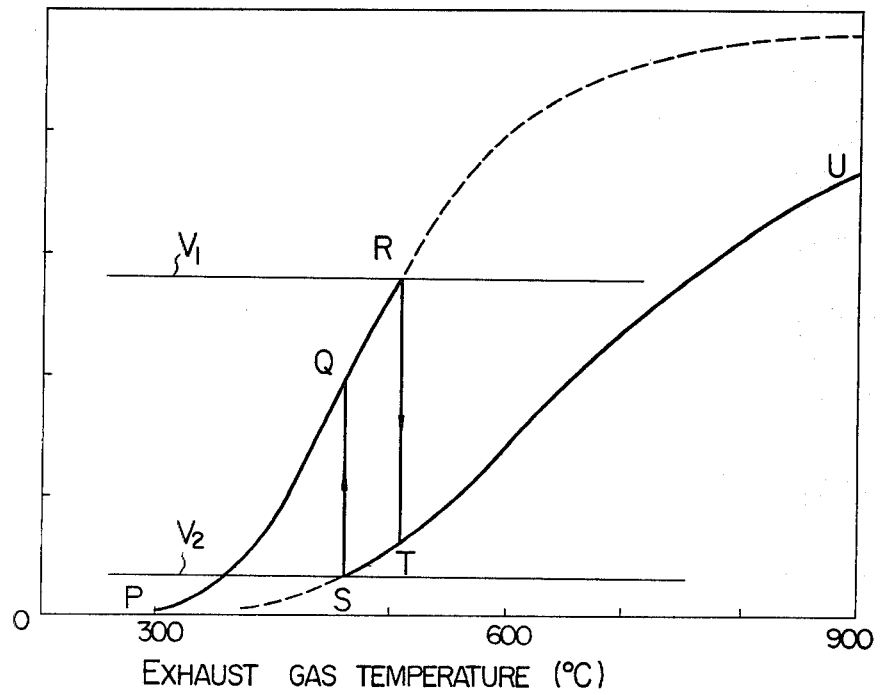
FIGS. 7 and 8 are graphs for explaining the operation of the present invention.

The lean side voltage of the voltage $V_A$ at the junction point is detected by the peak sample circuit 33. The detected minimum value, i.e., the lean-side peak voltage $V_L$ changes from P to Q and further to R as shown in FIG. 7 or such as $V_L$ shown in FIG. 8(a) in accordance with the change of the temperature of the exhaust gas. When the voltage $V_A$ reaches the point R, the voltage $V_L$ becomes higher than the preset voltage $V_1$ in the dividing voltage switching control circuit 36, therefore, as shown at time $t_1$ in FIG. 8(b), the output of the comparator 108 becomes "0", thus raising the output of the flip-flop 120 to "1" as shown in FIG. 8(d). As a result, the switch 103 is turned on, so that the electrical resistance value of the dividing resistor 31 connected to the air-fuel ratio sensor 20 becomes substantially equal to the resistance value of parallel resistors 101 and 102. Thus, the minimum value $V_L$ on the lean side of the voltage $V_A$ decreases from point R to point T. Further, in accordance with the increase in temperature, the peak voltage $V_L$ on the lean side of the voltage $V_A$ changes to point U.

Next, when the temperature of the exhaust gas begins to decrease, the lean-side peak voltage $V_L$ of the voltage $V_A$ changes from the point U to the point T and further to the point S. At the point S, the voltage $V_L$ becomes lower than the set voltage V2 of the dividing resistor switching control circuit 36 and therefore the output of the comparator 109 is raised to "1" level as shown at time t2 of FIG. 8(c). The output of the flip-flop 120 is reduced to "0" through the NOT circuit 110 as shown in FIG. 8(d), thus turning off the switch 103. As a result, only the resistor 101 of the dividing resistor 31 connected to the air-fuel ratio sensor 20 remains effective, so that the lean-side minimum value $V_L$ of the voltage $V_A$ at the junction point returns from the point S to the point Q.

Figure 3:
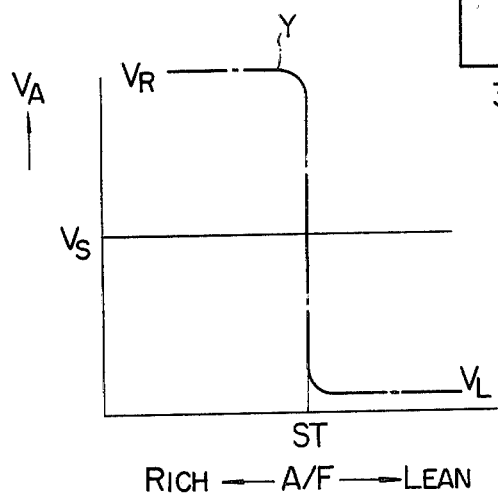
FIG. 3 is a graph showing the voltage at the junction point of the air-fuel ratio sensor and a dividing resistor connected in series thereto as the value of the dividing resistor is changed.

Thus, as shown in FIG. 8(a), even when the working temperature changes, the peak voltage $V_L$ on the lean side always remains smaller than the reference voltage Vs while the peak voltage $V_R$ on the rich side remains higher than the reference voltage Vs, so that the voltage $V_A$ changes across the reference voltage Vs when the air-fuel ratio changes. Therefore, even at the working temperature of 800° C. of the air-fuel ratio sensor 20, the voltage $V_A$ changes as shown by curve Y in FIG. 3, thus making it possible to detect the stoichiometric air-fuel ratio ST efficiently. In other words, when the resistance of the air-fuel ratio sensor 20 becomes to be the lean resistance value L, the voltage $V_A$ becomes smaller than the reference voltage Vs, and the comparator 130 of the comparator circuit 35 produces "1" level signal and the inverter 131 produces "0" level signal. When the resistance of the air-fuel ratio sensor 20 becomes to be the rich resistance value R, the voltage $V_A$ becomes higher than the reference voltage Vs, and the comparator circuit 130 produces "0" level signal and the inverter 131 produces "1" level signal.

In this way, regardless of the change over whole range of the electrical resistance Re depending on the working temperature etc. of the air-fuel ratio sensor 20, by means of the air-fuel ratio detection signal of "0" level produced from the comparator circuit 35 it can be determined that the actual air-fuel ratio of the mixture gas is higher than the stoichiometric value ST thereof, and by means of the air-fuel ratio detection signal of "1" level it can be discriminated that the air-fuel ratio is lower than the stoichiometric value ST thereof.

The air-fuel ratio detection signal is applied through a driving circuit not shown to the mixture gas supplier 12. When the air-fuel ratio detection signal is "0" level, the air-fuel ratio regulator of the mixture gas supplier 12 thickens the mixture gas thereby to reduce the air-fuel ratio, thus causing the air-fuel ratio to approach to the stoichio-metric value ST thereof.

When the air-fuel ratio detection signal is "1" level, on the other hand, the air-fuel ratio regulator of the mixture gas supplier 12 thins the mixture gas thereby to increase the air-fuel ratio, thus causing the air-fuel ratio to approach to the stoichiometric value ST.

Thus, the air-fuel ratio is always regulated at the stoichiometric air-fuel ratio ST accurately with the ternary catalyst converter 16 removing the NOx, HC and CO at high efficiency.

Figure 9:
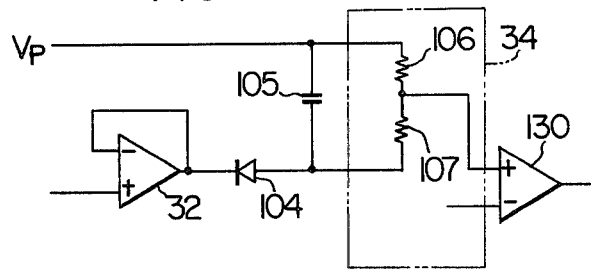
FIGS. 9 and 10 are diagrams showing electrical circuits of the essential parts of another embodiment of the present invention.

In the above-mentioned embodiment, the reference voltage Vs of the voltage generator circuit 34 is set at a constant value. But as shown in FIG. 9, the reference voltage may be set to have a value which lies at a point in a fixed proportion between the source voltage Vp and the lean minimum value $V_L$ by connecting the resistors 106 and 107 in parallel to the capacitor 105. Here, it is necessary to set the value within the range of variation of the voltage $V_A$ at the junction point to enable satisfactory detection of the stoichiometric air-fuel ratio ST.

Figure 10:
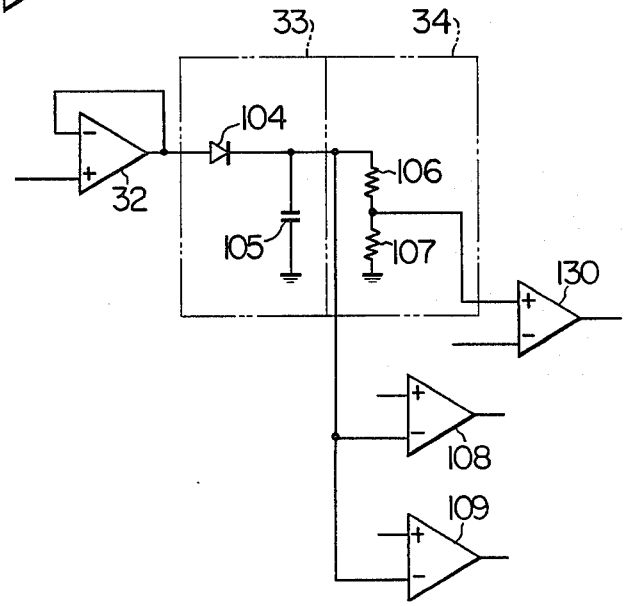

Also, in the above-mentioned embodiment, the dividing resistors are switched by detecting the peak voltage $V_L$ on the lean side of the voltage $V_A$ at the junction point. As an alternative, it may be arranged to make the values of the resistors 113, 114, 115 and 116 which are for setting the non-inversion terminal input voltages of the comparators 108 and 109 and the values of the dividing resistors 101 and 102 appropriate ones, and as shown in FIG. 10, make the peak sample circuit 33 a maximum detector circuit using diodes 104 and 105, while making the voltage generator circuit 34 to produce a voltage at a value intermediate the detection value of the sample circuit 33 and the grounding potential, so that the rich-side peak voltage $V_R$ of the potential $V_A$ at the junction point is detected for switching control of the dividing resistors.

Further, while in the above-mentioned embodiment the present invention is applied to the air-fuel ratio control system of the engine intake system. The present invention, however, may be also applied with equal effect to what is called the air-fuel ratio control system for the exhaust system for controlling the secondary air supplied to the exhaust system from the air-fuel ratio sensor 20.

Furthermore, in the above embodiment the air-fuel ratio sensor 20 is connected to the power supply side and the dividing resistor 101 is connected to the grounding side, but it may be constructed such that the air-fuel ratio sensor 20 is connected to the ground side and the dividing resistor 101 is connected to the power supply sides. In this case, if the buffer amplifier 32 is comprised of an inverted amplifier, the other circuits may be left unchanged.

We claim:

1. An air-fuel ratio detecting system for internal combustion engines comprising:
   oxygen detecting means disposed in an exhaust passage of an internal combustion engine for detecting an absence and presence of oxygen, said oxygen detecting means exhibiting a rich resistance and a lean resistance in response to said absence and presence of oxygen in said exhaust passage, respectively;
   variable resistance means connected in series with said oxygen detecting means;
   power supply means for supplying a series circuit of said oxygen detecting means and said variable resistance means with an electric power so that said series circuit develops a rich and a lean voltages in response to said rich resistance and said lean resistance of said oxygen detecting means, respectively, at a junction between said oxygen detecting means and said variable resistance means;
   reference comparison means for comparing said rich and lean voltages with a reference value so that an air-fuel ratio of mixture supplied to said internal combustion engine is detected;
   sampling means for sampling a peak value of predetermined one of said rich and lean voltages;
   first comparison means for comparing said sampled peak value with a pedetermined first value;
   second comparison means for comparing said sample peak value with a predetermined second value; and
   means for varying the resistance value of said variable resistance means in response to the output signals of said first and second comparison means so that one and the other of said rich and lean voltages are kept larger and smaller than said reference value.

2. A system according to claim 1 further comprising: means for varying said reference value in accordance with said sampled peak value.

* * * * *